(12) United States Patent
Takagi et al.

(10) Patent No.: US 12,245,867 B2
(45) Date of Patent: Mar. 11, 2025

(54) MEASURING DEVICE (71) Applicant: Murata Manufacturing Co., Ltd., Nagaokakyo (JP)

(72) Inventors: Jun Takagi, Nagaokakyo (JP); Tomoki Takahashi, Nagaokakyo (JP); Hiroaki Togashi, Nagaokakyo (JP); Kenji Tanaka, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 599 days.

(21) Appl. No.: 17/373,005

(22) Filed: Jul. 12, 2021

(65) Prior Publication Data
US 2021/0338143 A1    Nov. 4, 2021

Related U.S. Application Data (63) Continuation of application No. PCT/JP2020/008400, filed on Feb. 28, 2020.

(30) Foreign Application Priority Data

Mar. 1, 2019 (JP) ................................ 2019-037292

(51) Int. Cl.
*A61B 5/00* (2006.01)
*A61B 5/0537* (2021.01)

(52) U.S. Cl.
CPC ............ *A61B 5/4277* (2013.01); *A61B 5/682* (2013.01); *A61B 5/6835* (2013.01)

(58) Field of Classification Search
CPC ..... A61B 5/4277; A61B 5/682; A61B 5/6835; A61B 5/6843; A61B 5/0537
See application file for complete search history.

(56) References Cited

U.S. PATENT DOCUMENTS

2012/0203259 A1    8/2012    Saeki et al.
2013/0274566 A1   10/2013   Koyama et al.
(Continued)

FOREIGN PATENT DOCUMENTS

CN    108379738 A    8/2018
JP    2005-205041 A   8/2005
(Continued)

OTHER PUBLICATIONS

International Search Report issued for PCT/JP2020/008400, date of mailing Apr. 21, 2020.
(Continued)

*Primary Examiner* — Lynsey C Eiseman
*Assistant Examiner* — Christopher J Mutchler
(74) *Attorney, Agent, or Firm* — ArentFox Schiff LLP (57) ABSTRACT

A measuring device is provided with an improved contact property of a measuring surface of a sensor with respect to a surface of a target object. The measuring device includes a main body and a probe that has a head section at the distal end thereof and an arm section connecting the head section to the main body. The head section has a support portion, a measuring portion, and a coupling portion. The support portion is connected to the distal end of the arm section. The measuring portion has a first surface at which a measuring surface of a sensor is exposed and a thickness with the first surface as a datum plane. The coupling portion is disposed between and couples the measuring portion and the support portion. The coupling portion has a first connection portion connected to the measuring portion and a through hole.

19 Claims, 6 Drawing Sheets

(56) References Cited

U.S. PATENT DOCUMENTS

| | | | | |
|---|---|---|---|---|
| 2014/0052120 A1* | 2/2014 | Benscoter | ............... | A61L 29/02 606/41 |
| 2014/0343373 A1* | 11/2014 | Shimoyama | ............. | A61B 5/01 600/301 |
| 2015/0005603 A1* | 1/2015 | Liu | ...................... | A61B 5/1486 427/508 |
| 2015/0150479 A1 | 6/2015 | Kei et al. | | |
| 2015/0216471 A1* | 8/2015 | Goldstein | ............... | A61B 5/682 600/573 |
| 2016/0135728 A1* | 5/2016 | Furukawa | ............ | A61B 5/6843 600/300 |
| 2017/0165042 A1* | 6/2017 | Hillukka | ................ | A61B 5/682 |

FOREIGN PATENT DOCUMENTS

| | | | |
|---|---|---|---|
| JP | 2018191717 A | 12/2018 |
| WO | 2004028359 A1 | 4/2004 |
| WO | 2011030714 A1 | 3/2011 |
| WO | 2012042878 A1 | 4/2012 |
| WO | 2014027377 A1 | 2/2014 |

OTHER PUBLICATIONS

Written Opinion of the International Searching Authority issued for PCT/JP2020/008400, date of mailing Apr. 21, 2020.

\* cited by examiner

MEASURING DEVICE

CROSS REFERENCE TO RELATED APPLICATIONS

The present application is a continuation of PCT/JP2020/008400 filed Feb. 28, 2020, which claims priority to Japanese Patent Application No. 2019-037292, filed Mar. 1, 2019, the entire contents of each of which are incorporated herein by reference.

TECHNICAL FIELD

The present disclosure relates to a measuring device.

BACKGROUND

International Publication No. 2004/028359) hereinafter "Patent Document 1") discloses a measuring device that is configured to measure a target object while being held by a hand of a measurer, for example, an intra-oral moisture measuring device. The intra-oral moisture measuring device has an electrostatic-capacity-type sensor at the distal end of a probe. Moreover, a measuring surface of the sensor is pressed parallel to a measurement target surface such as a lingual mucosa, which is to be a target object, and the sensor measures the amount of the moisture of the target object.

In certain instances, some measurement target subjects, who are to be target objects, cannot smoothly stick their tongues out. For such measurement target subjects, there may be difficulty in inserting the distal end of the probe into the oral cavity or in causing the measuring surface of the sensor to be pressed parallel to the tongue in the oral cavity, with the above-described measuring device. When an angle is produced between the measuring surface of the sensor and the surface of the target object, the values of measurement results may vary.

SUMMARY OF THE INVENTION

According, it is an object of the present disclosure to provide a measuring device with an improved contact property of a measuring surface of a sensor with respect to a surface of a target object.

Thus, according to an exemplary aspect, a measuring device is disclosed that includes a main body and a probe. The probe has a head section at the distal end thereof and an arm section connecting the head section to the main body. The head section has a support portion connected to the distal end of the arm section; a measuring portion having a first surface at which a measuring surface of a sensor is exposed, with the measuring portion having a thickness with the first surface as a datum plane; and a coupling portion disposed between the measuring portion and the support portion and coupling the measuring portion to the support portion. Moreover, the coupling portion has a first connection portion connected to the measuring portion and a second connection portion connected to the support portion. The coupling portion has a through hole and is made of a soft material.

With the configuration, the measuring portion easily tilts relative to the support portion due to the coupling portion made of the soft material, and the contact property of the first surface of the measuring portion with respect to a measurement target surface of a target object is improved.

According to the exemplary measuring device described herein, the contact property of the measuring surface of the sensor with respect to the surface of the target object can be improved.

DETAILED DESCRIPTION OF EMBODIMENT

Figure 1A:
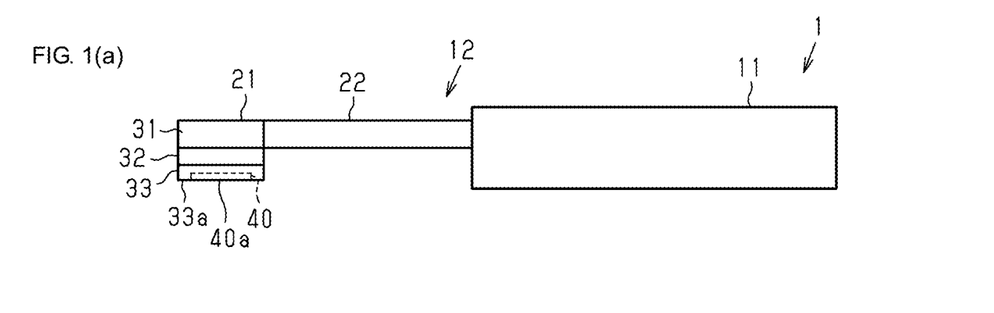
FIG. 1(a) is a schematic side view of a measuring device according to an embodiment.

Hereinafter, an exemplary embodiment will be described. A measuring device 1 illustrated in FIG. 1(a) is an intra-oral moisture measuring device configured to measure, for example, the amount of moisture in an oral cavity, which is a measurement target.

As shown, the measuring device 1 is substantially rod-shaped and has a main body 11 and a probe 12 arranged in the longitudinal direction.

The main body 11 has, for example, a substantially rectangular parallelepiped shape. It is noted that regarding the shape of the main body 11, the external shape of a section thereof orthogonal to the longitudinal direction can be a polygonal shape, a circular shape, an oval shape, or a shape formed by combining ones of the shapes according to alternative aspects. In addition, the main body 11 can also have different external sizes of the sections thereof orthogonal to the longitudinal direction.

The probe 12 has a head section 21 at the distal end thereof and an arm section 22 connecting the head section 21 to the main body 11.

The head section 21 has a support portion 31, a coupling portion 32, and a measuring portion 33 that are arranged in this order from top to bottom.

The support portion 31 has a substantially rectangular plate shape. The support portion 31 is connected to the distal end of the arm section 22. It is noted that the support portion 31 and the arm section 22 may be formed separately or may be formed as a single body. In addition, in FIG. 1(c), the arm section 22 has a width smaller than that of the measuring portion 33; however, the arm section 22 may alternatively have the same width as that of the measuring portion 33 or may have a width larger than that of the measuring portion 33 in alternative aspects.

Figure 1B:
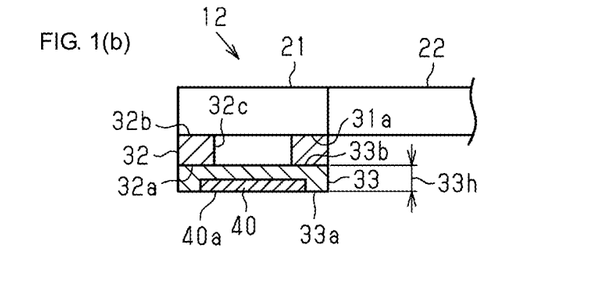
FIG. 1(b) is a partial sectional view of a probe.
Figure 1C:
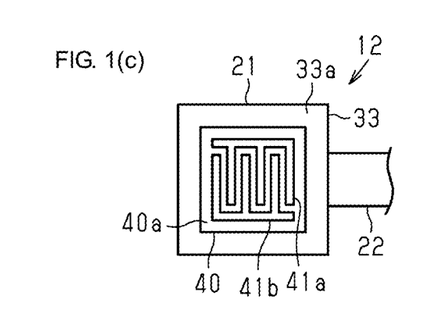
FIG. 1(c) is a partial plan view of the probe as viewed from a sensor surface.

FIG. 1(b) illustrates the measuring portion 33 having a first surface 33a and a thickness 33h with the first surface 33a as a datum plane. Moreover, the measuring portion 33 has, for example, a substantially rectangular plate shape. The measuring portion 33 has a second surface 33b on the opposite side to the first surface 33a. The measuring portion 33 has a sensor 40 with a flat plate shape and a flat measuring surface 40a. The sensor 40 is, for example, an electrostatic-capacity-type sensor. As shown in FIG. 1(b), the measuring surface 40a of the sensor 40 and the first surface 33a of the measuring portion 33 are flush with one another. As FIGS. 1(b) and (c), the measuring surface 40a of the sensor 40 is exposed at the first surface 33a of the measuring portion 33.

As FIG. 1(c), the measuring surface 40a of the sensor 40 has paired electrodes 41a and 41b. The paired electrodes 41a and 41b are each, for example, comb-shaped. The paired electrodes 41a and 41b function as the electrodes of a capacitor. That is, a measurement target and the liquid on the surface of the measurement target opposing to the measuring surface 40a function as dielectrics for the paired electrodes 41a and 41b. The capacitance value of the paired electrodes 41a and 41b is a value according to the amount of the moisture of the measurement target and the surface of the target.

Figure 1D:
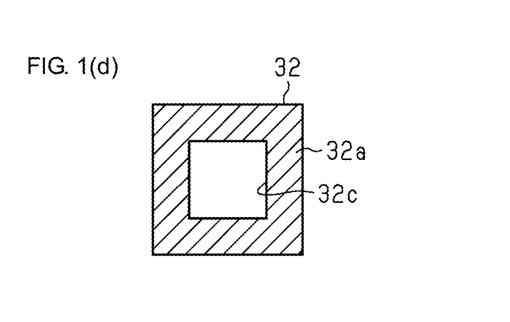
FIG. 1(d) is a plan view of a soft member.

As shown in FIGS. 1(a) and (b), the coupling portion 32 is interposed between the second surface 33b of the measuring portion 33 and a first surface 31a of the support portion 31 and couples the measuring portion 33 to the support portion 31. FIG. 1(d) illustrates the external shape of the coupling portion 32 according to the present embodiment that is a substantially rectangular frame shape, and the coupling portion 32 having a first connection portion 32a connected to the measuring portion 33 and a second connection portion 32b connected to the support portion 31. The first connection portion 32a is connected to the second surface 33b of the measuring portion 33 and formed by, for example, a plane. The second connection portion 32b is connected to the first surface 31a of the support portion 31 and constituted by, for example, a plane. The first connection portion 32a and the second connection portion 32b may be referred to as a first connection surface and a second connection surface, respectively, for purposes of this disclosure. In the example of FIG. 1(b), the first connection portion 32a and the second connection portion 32b are flat surfaces.

As further shown, the coupling portion 32 has a through hole 32c. In a direction perpendicular to the first surface 33a of the measuring portion 33, the through hole 32c passes through the coupling portion 32 from the first connection portion 32a to the second connection portion 32b in the thickness direction. The thickness of the coupling portion 32 in the direction perpendicular to the first surface 33a of the measuring portion 33 is uniform apart from the through hole 32c. In the present embodiment, the shape of the through hole 32c is rectangular as viewed in a layering direction of the measuring portion 33, the coupling portion 32, and the support portion 31 in the head section 21. It is noted that the layering direction in the head section 21 is the direction perpendicular to the first surface 33a of the measuring portion 33, that is, a direction perpendicular to the measuring surface 40a of the sensor 40.

According to the exemplary aspect, the through hole 32c is formed so that the line segment that passes the center of the first surface 33a of the measuring portion 33 and that is perpendicular to the first surface 33a is surrounded by the coupling portion 32. For example, the coupling portion 32 is formed so that the center of the measuring portion 33 and the center of the coupling portion 32 correspond to one another in the direction perpendicular to the first surface 33a or so that the center of gravity of the measuring portion 33 and the center of gravity of the coupling portion 32 correspond to one another in the direction perpendicular to the first surface 33a.

In the present embodiment, the coupling portion 32 is symmetrical as viewed in the direction perpendicular to the first surface 33a of the measuring portion 33. Examples of such a symmetrical shape include a shape having point symmetry with the center of the measuring portion 33 as the center of the symmetry and a shape having line symmetry about the axis that passes the center of the measuring portion 33 and is parallel to the first surface 33a.

According to the exemplary aspect, the coupling portion 32 is made of a soft material softer than the measuring portion 33 and the support portion 31. Examples of such a soft material include silicone, acryl, urethane, polyvinyl chloride, polyethylene, polystyrene, polypropylene, polycarbonate, and a Teflon®-based resin. The soft material preferably has a hardness E5 or more and A50 or less and more preferably has, for example, a hardness A30. Note that the support portion 31 is preferably made of a material softer than the measuring portion 33. In addition, regarding a method of measuring a hardness, an evaluation is performed by using durometers based on ISO (International Organization for Standardization) or the newly established and revised JIS as measuring instruments. A load is applied to a needle-shaped indenter, and a hardness is quantified from the indentation depth of the indenter with respect to a balloon.

In an exemplary aspect, a wire, which is not illustrated, is inserted into the through hole 32c. The sensor 40 is connected to a circuit board by using the wire. Components such as an oscillation circuit and a control circuit are mounted on the circuit board. The oscillation circuit outputs a signal of the frequency corresponding to, for example, the capacitance value of the sensor 40. The control circuit detects the amount of the moisture of a measurement target, based on the output signal of the oscillation circuit. The control circuit then displays the detected moisture amount on a display, which is not illustrated, provided on the main body 11. The circuit board is built in, for example, the main body 11. It is noted that plural circuit boards may be provided in the measuring device 1. The plural circuit boards are disposed in the head section 21 or the arm section 22 or disposed in the head section 21 and the arm section 22.

(Function)

Next, the function or operation of the above-described measuring device 1 will be described.

Figure 2A:
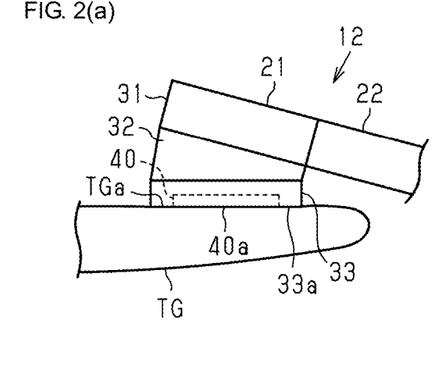
FIG. 2(a) and FIG. 2(b) are partial enlarged views of the probe and illustrate the function of the measuring device.
Figure 2B:
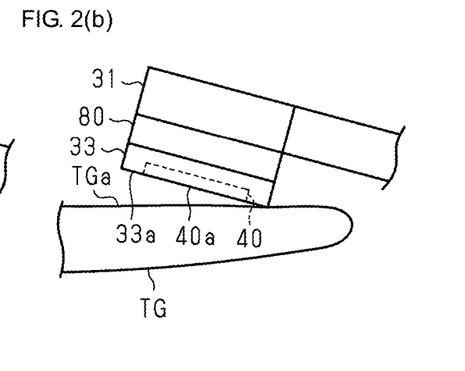

A measurer grasps the main body 11 of the measuring device 1. As shown in FIG. 2(a), the measurer presses the first surface 33a of the measuring portion 33 at the distal end of the probe 12 against a measurement target surface TGa of a target object TG. The target object TG is, for example, a tongue of a user or patient. At this point, the coupling portion 32 between the measuring portion 33 and the support portion 31 is made of a soft material. Thus, the coupling portion 32 is configured to easily deform and the measuring portion 33 thereby tilts relative to the support portion 31. As a result, the entire first surface 33a of the measuring portion 33 easily comes into contact with the measurement target surface TGa of the target object TG. For example, as FIG. 2(b) illustrates, in the case where a coupling portion 80 made of a hard material is used and does not deform, when the measuring portion 33 comes into contact with the target object TG obliquely, a gap is formed between the first surface 33a of the measuring portion 33 and the measurement target surface TGa of the target object TG, and the accuracy of measurement decreases. It is noted that the same applies to the case where the measuring portion 33 is directly connected to the support portion 31. In contrast, in the measuring device 1 according to the present embodiment, the contact property of the first surface 33a of the measuring portion 33 with respect to the measurement target surface TGa of the target object TG is improved. Consequently, the accuracy of measurement can be increased.

The coupling portion 32 has the through hole 32c. Thus, the coupling portion 32 is likely to deform uniformly at each side of the rectangular measuring portion 33. On this account, the contact property of the first surface 33a of the measuring portion 33 with respect to the measurement target surface TGa of the target object TG is improved, and the accuracy of measurement can be increased.

The through hole 32c is formed so that the line segment that passes the center of the first surface 33a of the measuring portion 33 and that is perpendicular to the first surface 33a is surrounded by the coupling portion 32. In this case, because the force applied to the first surface 33a of the measuring portion 33 is efficiently dispersed in the coupling portion 32 made of a soft material, the contact property of the first surface 33a of the measuring portion 33 with respect to the measurement target surface TGa of the target object TG is improved, and the accuracy of measurement is also increased.

In addition, the support portion 31 is preferably made of a material softer than the measuring portion 33 to increase the accuracy of measurement. For example, if the measuring portion 33 is soft, the distance between the electrodes 41a and 41b of the sensor 40 changes, and the measurement variation is increased. If the support portion 31 is harder than the measuring portion 33, a pressing force is hardly applied uniformly to the first surface 33a, and the measurement variation is increased.

As described above, the following advantageous effects are exhibited according to the present embodiment.

The measuring device 1 has the main body 11 and the probe 12. The probe 12 has the head section 21 at the distal end thereof and the arm section 22 connecting the head section 21 to the main body 11. The head section 21 has the support portion 31, the measuring portion 33, and the coupling portion 32. The support portion 31 is connected to the distal end of the arm section 22. The measuring portion 33 has the first surface 33a at which the measuring surface 40a of the sensor 40 is exposed. The measuring portion 33 has the thickness 33h with the first surface 33a as a datum plane. The coupling portion 32 is disposed between the measuring portion 33 and the support portion 31 and couples the measuring portion 33 and the support portion 31 to one another. The coupling portion 32 has the first connection portion 32a connected to the measuring portion 33 and the second connection portion 32b connected to the support portion 31. The coupling portion 32 has the through hole 32c and is made of a soft material.

With the configuration, the coupling portion 32 made of a soft material easily deforms when the first surface 33a of the measuring portion 33 at the distal end of the probe 12 is pressed against the measurement target surface TGa of the target object TG. Thus, the contact property of the first surface 33a of the measuring portion 33 with respect to the measurement target surface TGa is improved, and the accuracy of measurement can be increased.

By having the thickness 33h with the first surface 33a as a datum plane, the measuring portion 33 has an advantage in transmitting, to the coupling portion 32, the magnitude and the direction of the pressing reaction force applied from the measurement target surface TGa. The coupling portion 32 elastically deforms according to the magnitude and the direction of the pressing reaction force applied from the measurement target surface TGa, and the following property of the first surface 33a of the measuring portion 33 with respect to the measurement target surface TGa can be improved.

Moreover, the thickness 33h of the measuring portion 33 can be set so that the elastic deformation of the measuring portion 33 when the first surface 33a of the measuring portion 33 is pressed against the measurement target surface TGa of the target object TG, that is, for example, bending and nonuniform compression of the measuring portion 33 are reduced or suppressed from occurring. When the elastic deformation of the measuring portion 33 is reduced or suppressed from occurring, there is an advantage in suppressing the measuring surface 40a of the sensor 40 from bending or twisting.

The coupling portion 32 has the through hole 32c. Thus, the deformation of the coupling portion 32 is likely to be uniform at each side of the rectangular measuring portion 33. On this account, the contact property of the first surface 33a of the measuring portion 33 with respect to the measurement target surface TGa of the target object TG is improved, and the accuracy of measurement can be increased.

The through hole 32c is formed so that the line segment that passes the center of the first surface 33a of the measuring portion 33 and that is perpendicular to the first surface 33a is surrounded by the coupling portion 32. In this case, because the force applied to the first surface 33a of the measuring portion 33 is efficiently dispersed in the coupling portion 32 made of a soft material, the contact property of the first surface 33a of the measuring portion 33 with respect to the measurement target surface TGa of the target object TG is improved, and the accuracy of measurement is also increased.

It is noted that the above-described embodiment can be implemented as follows in refinements of the exemplary aspect.

Regarding the above-described embodiment, the shape of the coupling portion 32 can be changed appropriately.

Figure 3A:
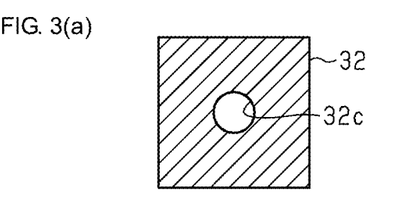
FIGS. 3(a) to 3(e) are plan views of soft members according to respective modifications.
Figure 3B:
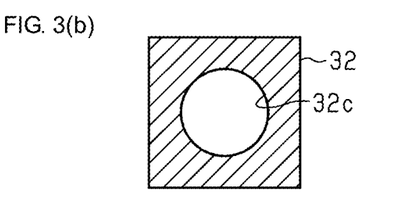

As shown in FIG. 3(a), the through hole 32c may alternatively have a circular shape, and, in addition, the size of the through hole 32c may be changed appropriately as shown in FIG. 3(b).

Figure 3C:
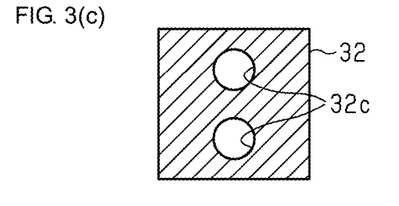
Figure 3D:
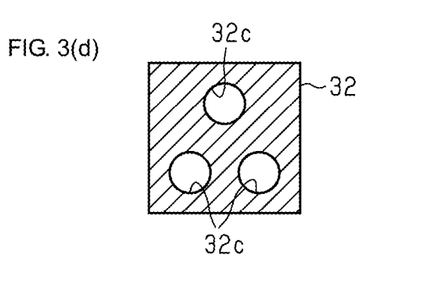
Figure 3E:
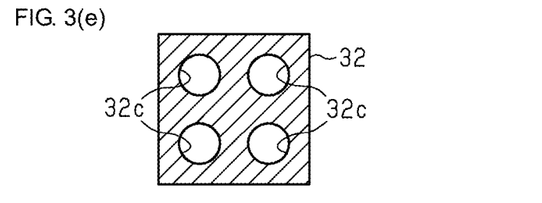

FIGS. 3(c), (d) and (e) illustrate a plurality of through holes 32c. The arrangement positions of the plural through holes 32c may be, for example, point symmetrical positions about the center of the coupling portion 32 as shown in FIGS. 3(c) and (e) and may also be line symmetrical positions with the line segment passing the center as the axis as shown in FIG. 3(a) to (e).

The deformation state of the coupling portion 32 can be set and adjusted by changing the number of the through holes 32c or the arrangement position of the through hole 32c, and, for example, how easily the measuring portion 33 is configured to tilt relative to the support portion 31 can be adjusted.

Figure 4:
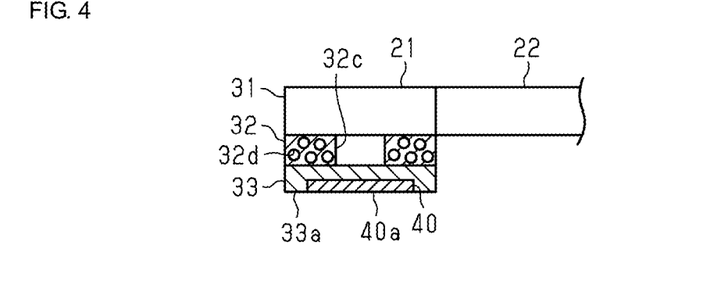
FIG. 4 is a partial sectional view of a probe and illustrates a soft member according to a modification.

As FIG. 4 illustrates, the coupling portion 32 can alternatively be a porous body having pores 32d there inside.

Thus, the coupling portion 32 easily deforms. On this account, the contact property with respect to the first surface 33a of the measuring portion 33 is improved, and the accuracy of measurement can be increased.

Figure 5:
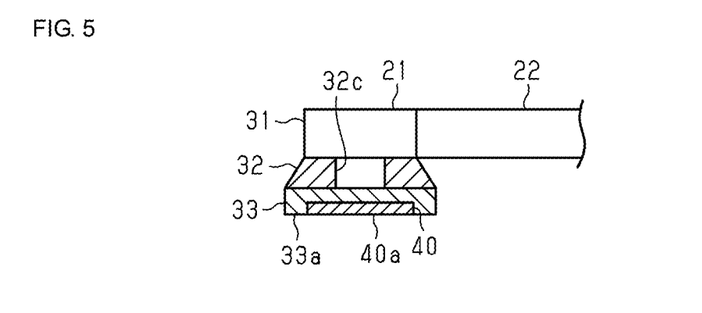
FIG. 5 is a partial sectional view of a probe and illustrates a soft member according to a modification.
Figure 6:
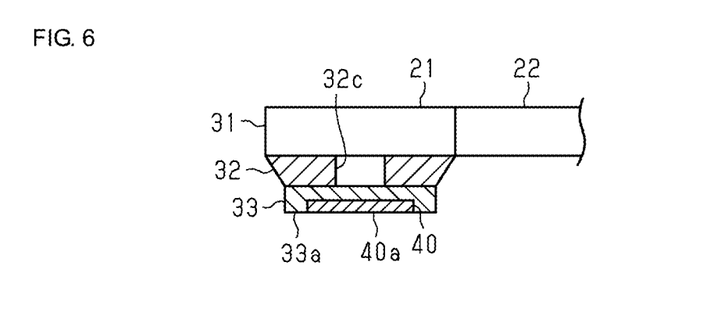
FIG. 6 is a partial sectional view of a probe and illustrates a soft member according to a modification.

As FIG. 5 illustrates, the coupling portion 32 can have an external size increasing as extending from the support portion 31 toward the measuring portion 33. Alternatively, as FIG. 6 illustrates, the coupling portion 32 can have an external size decreasing as extending from the support portion 31 toward the measuring portion 33. The coupling portion 32 greatly deforms due to the pressing force pressing the measuring portion 33 against the target object TG, the contact property of the first surface 33a of the measuring portion 33 with respect to the measurement target surface TGa of the target object TG is improved, and the accuracy of measurement can be increased.

A modification will be described with reference to FIG. 7. The Z direction illustrated in the rectangular coordinate system in FIG. 7 indicates the thickness direction of a head section 21 or a measuring portion 33. The X direction indicates the length direction of the head section 21 or the measuring portion 33. The Y direction indicates the width direction of the head section 21 or the measuring portion 33. The XY plane is an example of an in-plane direction of the measuring portion 33 or a measuring surface 40a. Each of the X direction and the Y direction is sometimes referred to as the lateral direction of the measuring portion 33.

Figure 7:
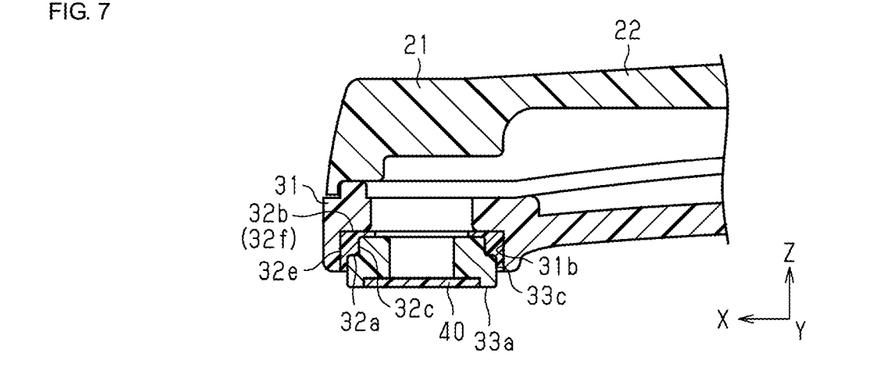
FIG. 7 is a partial sectional view of a probe according to a modification.

In the example of FIG. 7, the measuring portion 33 has a side surface 33c extends while intersecting or being orthogonal to a first surface 33a of the measuring portion 33. The side surface 33c of the measuring portion 33 is formed as the outer peripheral surface or the laterally outward-oriented surface of the measuring portion 33. The side surface 33c of the measuring portion 33 may be formed as, for example, a step surface.

A first connection portion 32a of a coupling portion 32 is formed so as to be in contact with at least a portion of the side surface 33c of the measuring portion 33. The first connection portion 32a of the coupling portion 32 can include a step surface corresponding to or fitting exactly on the side surface 33c of the measuring portion 33. For example, the coupling portion 32 has an annular or tubular shape and has the inner peripheral surface or the laterally inward-oriented surface of a through hole 32c and the outer peripheral surface or the laterally outward-oriented surface. Moreover, the inner peripheral surface of the coupling portion 32 is formed so as to be in contact with at least a portion of the side surface 33c of the measuring portion 33, for example, along the entire periphery of the portion. The contact area between the measuring portion 33 and the coupling portion 32 is increased by the side surface 33c of the measuring portion 33 being in contact with the coupling portion 32. At the time of measurement, the elastic resilient force of the coupling portion 32 in the lateral direction acts upon the side surface 33c of the measuring portion 33, and the lateral positional shifting of the measuring portion 33 can be suppressed from being caused in measuring.

The measuring portion 33 can have a sensor 40 and a sensor-mounting component supporting or holding the sensor 40. The sensor-mounting component has a sensor-seated surface on which the sensor 40 is mounted and is formed as, for example, a molded synthetic resin component.

In the example of FIG. 7, a support portion 31 is formed so as to surround a side surface 32e of the coupling portion 32 (for example, the outer peripheral surface of the coupling portion 32). For example, the support portion 31 can have an accommodation portion or a first recess 31b that is formed so as to accommodate a portion or the entire coupling portion 32 in the thickness direction. The first recess 31b may have an opening that corresponds to or is identical to the projected shape of the coupling portion 32 in the thickness direction, and the first recess 31b may have a depth from the opening. The side surface 32e of the coupling portion 32 is in contact with the support portion 31. The side surface 32e of the coupling portion 32 may be formed so as to be in contact with the inner peripheral surface of the first recess 31b of the support portion 31 along the entire periphery. The side surface 32e of the coupling portion 32 is in contact with the support portion 31 that is harder than the coupling portion 32 or more unlikely to elastically deform than the coupling portion 32, and it is thereby possible to suppress the measuring portion 33 from laterally moving and to suppress the lateral positional shifting of the measuring portion 33 in measuring, from being caused.

A second connection portion 32b of the coupling portion 32 can include an upper surface 32f of the coupling portion 32. The upper surface 32f of the coupling portion 32 included in the second connection portion 32b is formed so as to be in contact with the bottom of the first recess 31b of the support portion 31. The upper surface 32f of the coupling portion 32 may be formed as, for example, an annular flat surface. The coupling portion 32 is disposed between the measuring portion 33 and the support portion 31 in the thickness direction and in the lateral direction. With the configuration, the coupling portion 32 can elastically deform in the thickness direction and/or the lateral direction according to the magnitude and the direction of the pressing reaction force applied when the measuring portion 33 is pressed against the target object TG, the following property for the displacement of the measuring portion 33 can be improved, and the contact property of the first surface 33a of the measuring portion 33 with respect to the measurement target surface TGa of the target object TG can be improved.

Figure 8A:
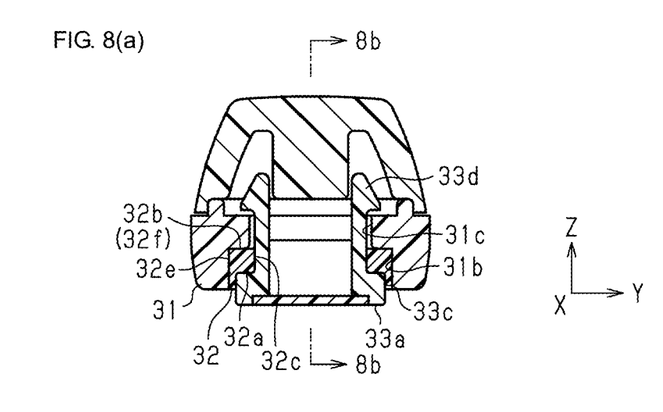
In FIG. 8(a) is a partial sectional view of a probe according to a modification of the exemplary embodiment and FIG. 8(b) is a sectional view taken along line 8b-8b in FIG. 8(a).
Figure 8B:
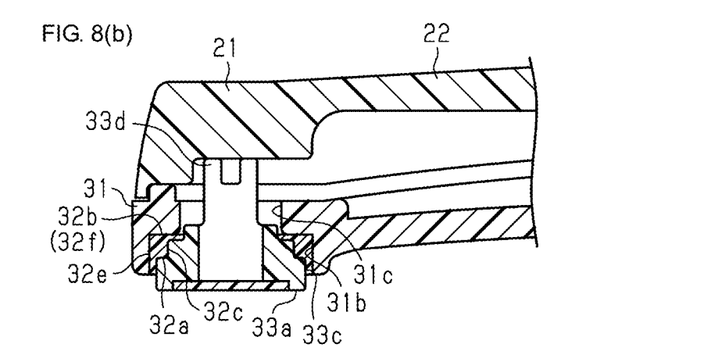
Figure 9:
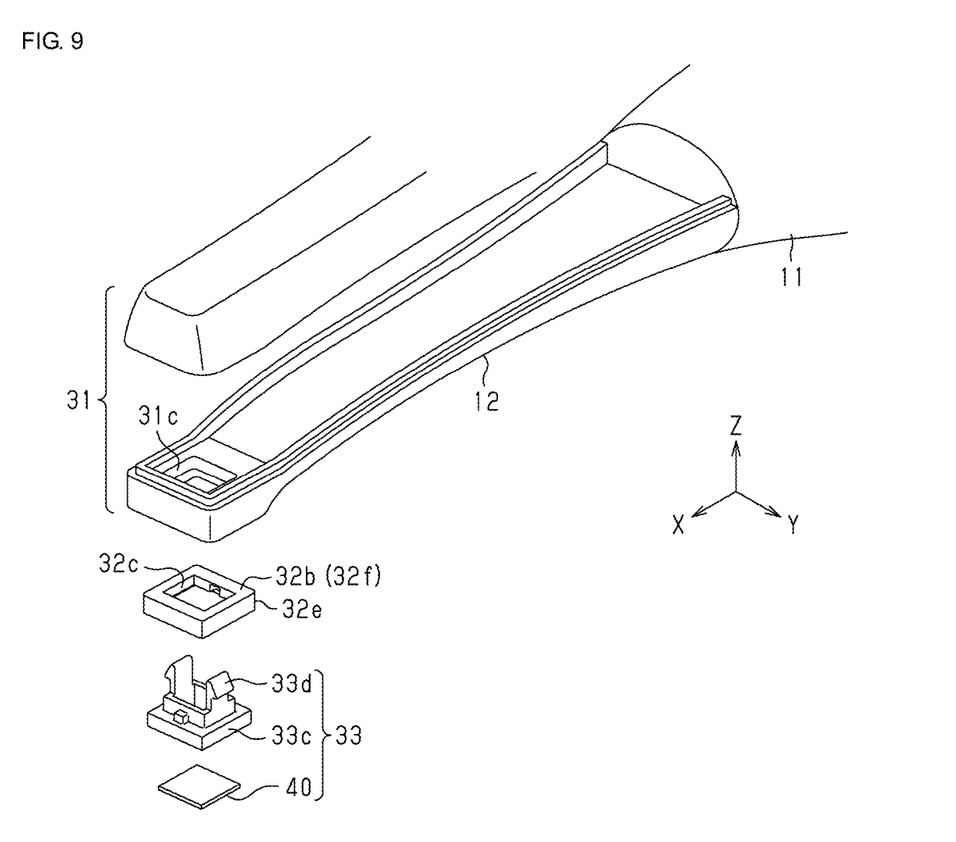
FIG. 9 is a schematic exploded perspective view of the probe in FIG. 8.
Figure 10:
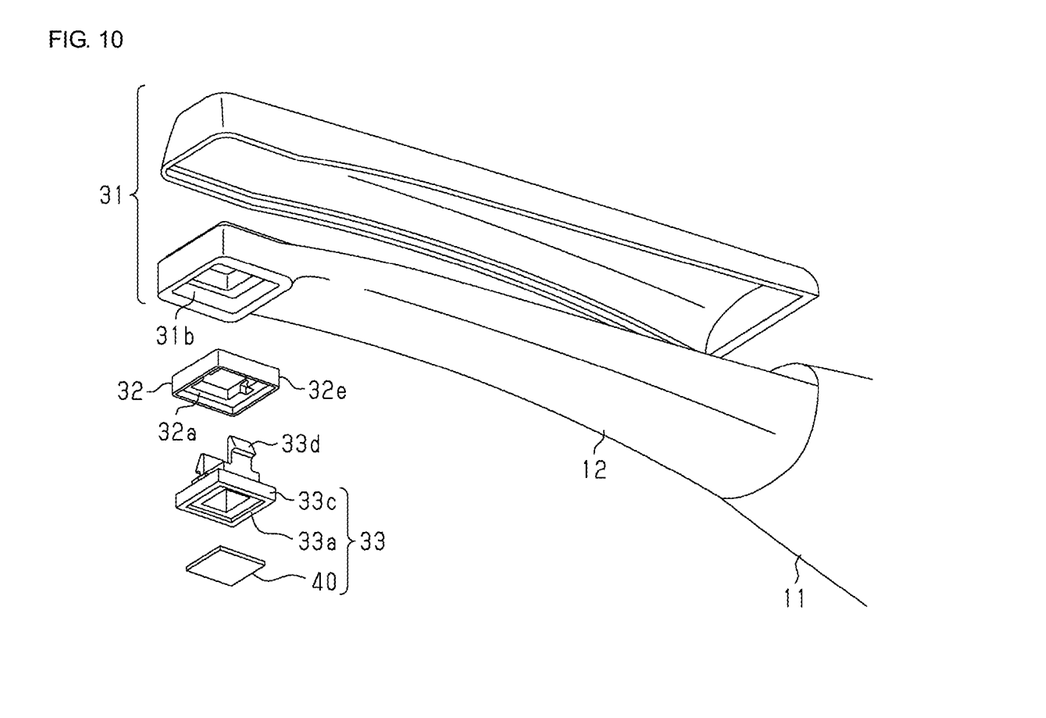
FIG. 10 is a schematic exploded perspective view of the probe in FIG. 8.

Regarding the modifications of FIGS. 8(a)-(b) to 10, differences from FIG. 7 will mainly be described. In the example of FIGS. 8(a) and (b), the shapes of a measuring portion 33 and a support portion 31 differ from those of the example of FIG. 7.

As FIGS. 8(a) and (b) illustrate, the measuring portion 33 has a fixing portion 33d on the opposite side to a first surface 33a in the thickness direction of the measuring portion 33. The support portion 31 has a second recess 31c into which the fixing portion 33d of the measuring portion 33 is fitted. Moreover, a coupling portion 32 is disposed between the measuring portion 33 and the support portion 31 with the fixing portion 33d of the measuring portion 33 being fitted into the second recess 31c of the support portion 31. The fixing portion 33d is fitted into the second recess 31c of the support portion 31, thereby being suppressed from laterally moving within the second recess 31c of the support portion 31, and the measuring portion 33 can be suppressed from laterally moving.

The fixing portion 33d and the second recess 31c can be configured so that the measuring portion 33 is movable relative to the support portion 31 at least in the thickness direction. In this exemplary embodiment, the fixing portion 33d is accommodated in the second recess 31c of the support portion 31 and is formed as a hook that is engaged with the support portion 31. The first recess 31b and the second recess 31c of the support portion 31 may be continuously formed or may be communicate with one another. The support portion 31 may have a step or an engaged surface that is formed between the first recess 31b and the second recess 31c. The fixing portion 33d of the measuring portion 33 may engage with the engaged surface of the support portion 31. Due to the engagement between the fixing portion 33d and the support portion 31, the measuring portion 33 can be suppressed from falling off the support portion 31.

Without the measuring portion 33 being pressed against the target object TG, the coupling portion 32 is held between the measuring portion 33 and the support portion 31 in a state of being compressed or not being compressed. When the measuring portion 33 is pressed against the target object TG, the fixing portion 33d of the measuring portion 33 is displaced within the second recess 31c of the support portion 31 at least in the thickness direction, and the coupling portion 32 is compressed between the measuring portion 33 and the support portion 31. The orientation of the measuring portion 33 changes according to the direction of the pressing reaction force when the measuring portion 33 is pressed against the target object TG, and the contact property of the first surface 33a of the measuring portion 33 with respect to the measurement target surface TGa of the target object TG can be improved.

Figure 11:
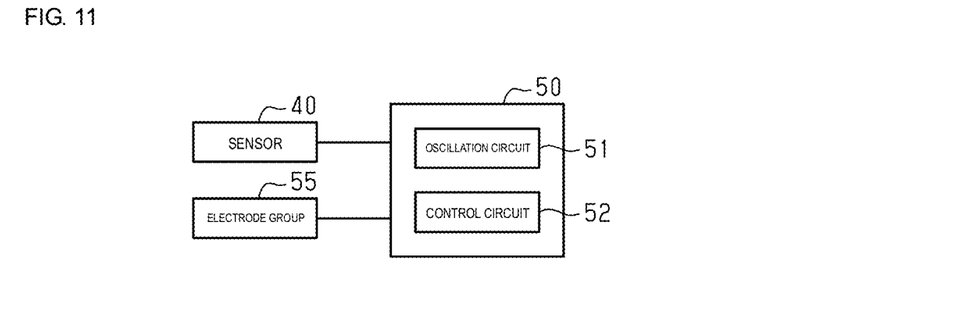
FIG. 11 is a block diagram of an electric circuit.

In the above-described embodiment and each modification, the coupling portion 32 can have two or more electrodes spaced and arranged vertically or laterally. Such two or more electrodes may be configured so as to output an output value according to at least one of the electrostatic capacity, the resistance value, and the magnetism that are associated with the expansion and contraction of the coupling portion 32 or an output value according to a change in at least one of the electrostatic capacity, the resistance value, and the magnetism that are associated with the expansion and contraction of the coupling portion 32. For example, as FIG. 11 illustrates, an electrode group 55 of the coupling portion 32 is connected to a circuit board 50 having components such as an oscillation circuit 51 and a control circuit 52. The control circuit 52 can be configured so as to detect the load applied when the measuring surface 40a is pressed against a measurement target, based on an output value of two or more electrodes 55 of the coupling portion 32. The control circuit 52 can be configured so as to perform at least one of the start of measurement and the correction of a measured value that are based on a signal of the sensor 40, according to the detected output value of the two or more electrodes 55 of the coupling portion 32. In an exemplary aspect, the control circuit 52 includes one or more memories storing computer-readable instructions and one or more processors configured to execute the computer-readable instructions. The control circuit 52 can be an integrated circuit such as an application-specific IC.

The sensor 40 can also protrude from the first surface 33a of the measuring portion 33.

Although the measuring device that measures the amount of moisture in an oral cavity is described in each of the above-described embodiment and modifications, the amount of moisture may be measured outside the oral cavity.

Although the measuring device in each of the above-described embodiment and modifications measures the amount of moisture, the measuring device may measure other quantities, degrees, and the like. For example, the measuring device may be a measuring device such as a pH meter or an oral bacteria measuring device in alternative aspects. Moreover, the measuring device may measure blood flow or the oxygen in blood. Furthermore, the measuring device may obtain plural kinds of values to be measured. On that occasion, it goes without saying that the electrostatic-capacity-type sensor according to the above-described embodiment is used as a sensor for a measurement target.

REFERENCE SIGNS LIST 1 measuring device
11 main body
12 probe
21 head section
22 arm section
31 support portion
32 coupling portion
32a first connection portion
32b second connection surface
32c through hole
32d pore
33 measuring portion
33a first surface
33b second surface
40 sensor
40a measuring surface

The invention claimed is:

1. A measuring device comprising:
a main body; and
a probe having a head section at a distal end thereof and an arm section that connects the head section to the main body,
wherein the head section includes:
a support portion connected to a distal end of the arm section;
a measuring portion having a first surface that exposes a flat measuring surface of a sensor having a flat plate shape, such that the flat measuring surface is flush with the first surface of the measuring portion; and
a coupling portion that couples the measuring portion to the support portion and is disposed therebetween,
wherein the coupling portion has a first connection portion connected to the measuring portion and a second connection portion connected to the support portion,
wherein the coupling portion is annular or tubular shaped to define a single through hole that extends continuously from the measuring portion to the support portion, the coupling portion being made of a material that is softer than a material of at least one of the measuring portion and the support portion, and
wherein the coupling portion comprises a porous body having a plurality of pores.

2. The measuring device according to claim 1,
wherein the measuring portion has a second surface on an opposite side to the first surface, and
wherein each of the first connection portion and the second connection portion of the coupling portion is comprised of a plane.

3. The measuring device according to claim 1, wherein the coupling portion has a plurality of the through holes.

4. The measuring device according to claim 1, wherein the coupling portion is formed to have line symmetry or point symmetry as viewed in a direction orthogonal to the measuring surface.

5. The measuring device according to claim 1, wherein a thickness of the coupling portion in a direction orthogonal to the measuring surface is uniform apart from the through hole.

6. The measuring device according to claim 1, wherein the coupling portion has an external size that increases as the coupling portion extends from the support portion towards the measuring portion.

7. The measuring device according to claim 1, wherein the coupling portion has an external size that decreases as the coupling portion extends from the support portion towards the measuring portion.

8. The measuring device according to claim 1, wherein the coupling portion has two or more electrodes spaced and arranged vertically or laterally.

9. The measuring device according to claim 8, wherein the two or more electrodes are configured to detect a load applied when the measuring surface is pressed against a measurement target, based on a change in at least one of an electrostatic capacity, a resistance value, and magnetism associated with expansion and contraction of the coupling portion.

10. The measuring device according to claim 9, further comprising a control circuit configured to perform at least one of a start of measurement and a correction of a measured value based on an output value of the two or more electrodes.

11. The measuring device according to claim 1, wherein the measuring portion has a side surface, and at least a portion of the side surface of the measuring portion contacts with the coupling portion.

12. The measuring device according to claim 11, wherein the coupling portion has a side surface that contacts the support portion.

13. The measuring device according to claim 11, wherein the support portion has a recess, and wherein the measuring portion has a fixing portion on an opposite side to the first surface in a thickness direction of the measuring portion, and the fixing portion is fitted into the recess of the support portion.

14. The measuring device according to claim 1, wherein the measuring device is configured as an intra-oral sensing device for detecting an amount of moisture in an oral cavity.

15. The measuring device according to claim 1, wherein the through hole of the coupling portion extends entirely therethrough.

16. The measuring device according to claim 1, wherein an external size of the coupling portion is larger than or equal to an external size of the measuring surface.

17. The measuring device according to claim 1, wherein the material forming the support portion is softer than the material forming the measuring portion.

18. The measuring device according to claim 1, wherein the material forming the coupling portion is softer than both the material forming the measuring portion and the material forming the support portion.

19. The measuring device according to claim 1, wherein the material of the coupling portion comprises at least one of silicone, acryl, urethane, polyvinyl chloride, polyethylene, polystyrene, polypropylene, polycarbonate, and a Teflon®-based resin.

* * * * *